United States Patent [19]

Kee et al.

[11] Patent Number: 5,445,141
[45] Date of Patent: Aug. 29, 1995

[54] RESPIRATORY SUPPORT SYSTEM

[75] Inventors: Kok-Hiong Kee; James G. Schneider, both of St. Louis; Gene B. Kartchner, Chesterfield, all of Mo.

[73] Assignee: Sherwood Medical Company, St. Louis, Mo.

[21] Appl. No.: 230,651

[22] Filed: Apr. 21, 1994

Related U.S. Application Data

[63] Continuation-in-part of Ser. No. 962,755, Oct. 19, 1992, Pat. No. 5,333,607.

[51] Int. Cl.⁶ ............................................. A61M 39/06
[52] U.S. Cl. ........................ 128/203.12; 128/204.18; 128/207.14; 604/268
[58] Field of Search ................. 128/203.12, 204.18, 128/207.16, 207.14; 604/268, 283, 284, 266–269, 905, 256, 249, 167

[56] References Cited

U.S. PATENT DOCUMENTS

| | | | |
|---|---|---|---|
| 1,588,336 | 6/1926 | Richmond | 285/331 X |
| 3,416,567 | 12/1968 | Von Dardel et al. | 137/604 |
| 3,528,427 | 9/1970 | Sheridan | 604/268 |
| 3,590,820 | 7/1971 | Nehra et al. | 604/268 |
| 4,182,343 | 1/1980 | Inaba | 604/268 |
| 4,240,417 | 12/1980 | Holever | 128/203.12 |
| 4,346,702 | 8/1982 | Kubota | 128/207.14 |
| 4,351,328 | 9/1982 | Bodai | 128/202.16 |
| 4,426,062 | 1/1984 | Bowron | 251/7 |
| 4,510,933 | 4/1985 | Wendt | 128/207.14 |
| 4,569,344 | 2/1986 | Palmer | 128/207.16 |
| 4,781,702 | 11/1988 | Herrli | 604/244 |
| 4,805,611 | 2/1989 | Hodgkins | 128/207.14 |
| 4,836,199 | 6/1989 | Palmer | 128/207.16 |
| 4,850,350 | 7/1989 | Jackson | 128/207.16 |
| 4,857,062 | 8/1989 | Russell | 604/256 |
| 4,950,232 | 8/1990 | Ruzicka et al. | 604/268 |
| 4,951,661 | 8/1990 | Sladek | 128/202.27 |
| 5,009,391 | 4/1991 | Steigerwald | 251/149.1 |
| 5,083,561 | 1/1992 | Russo | 128/207.16 |
| 5,158,569 | 10/1992 | Strickland | 604/283 |
| 5,215,522 | 6/1993 | Page et al. | 604/33 |
| 5,333,607 | 8/1994 | Kee et al. | 128/204.18 |

Primary Examiner—Edgar S. Burr
Assistant Examiner—William J. Deane, Jr.
Attorney, Agent, or Firm—Andrew J. Beck; Montgomery W. Smith; Gene B. Kartchner

[57] ABSTRACT

The invention relates to a respiratory support system (10) which includes a suction catheter device (41), a suction control valve (36), and a ventilator manifold (11). The ventilator (11) includes an access port (15) for attachment and detachment of the suction catheter device (41) thereto without interruption of continuous respiratory support of the patient. The access port (15) has a normally closed valve (16) therein which remains closed regardless of the pressure changes within the manifold (11). The normally closed valve (16) is positioned in the port (15) such that placement of a specially designed connector (40) of the suctioning device (41) therein forces the normally closed valve (16) to an open position, The manifold (11) and valve (16) are adapted to allow cleaning of the catheter (54) therethrough without detachment thereof.

12 Claims, 8 Drawing Sheets

RESPIRATORY SUPPORT SYSTEM

This application is a continuation-in-part of U.S. patent application Ser. No. 962,755 filed Oct. 19, 1992, now U.S. Pat. No. 5,333,607 for "Ventilator Manifold with Accessory Access Port".

BACKGROUND OF THE INVENTION

1. Field of the Invention

This invention relates generally to apparatus used in conjunction with a respiratory support system. More specifically, the present invention relates to a method and apparatus for using a suction catheter device as part of a respiratory support system. Even more specifically, the present invention relates to the attachment and detachment of a suction catheter device from a ventilator manifold used with a respiratory support system without interruption or loss of continuous respiratory support of a patient and with interattachment structure allowing for cleaning of the catheter through the manifold.

2. Prior Art

Respiratory support systems used for the ventilation of critically ill patients are now commonly used in medical facilities. Typically, a prior art respiratory support system includes a tracheal tube positioned either directly, or through the nose or mouth, into the trachea of a patient, a manifold connected to the tracheal tube at one port position thereof, and a source of breathable gas connected at a second port thereof. The purpose of the respiratory support system is to assist the patient in maintaining adequate blood oxygenation levels without overtaxing the patient's heart and lungs.

While a patient is attached to the respiratory support system, it is periodically necessary to aspirate fluid from the patient's trachea or lungs. In the past, in order to accomplish aspiration, it has been necessary to disassemble part of the respiratory support system, either by removing the ventilator manifold therefrom or by opening a port of the manifold and inserting a small diameter suction tube down the tracheal tube and into the patient's trachea and lungs. The fluid was then suctioned from the patient and the suction catheter was removed and the respiratory support system reassembled. However, due to the interruption of respiratory support during this procedure, a patient's blood oxygen often dropped to an unacceptably low level, even when other previously known breathing assistance efforts were simultaneously provided.

One solution to the above problem, which is generally exemplary of the prior art, is shown in U.S. Pat. No. 5,073,164 to Hollister et al., which includes a ventilator manifold having an access port therethrough which is adapted to receive a connector of the suction catheter device. The suction catheter device positions a catheter within the ventilator manifold without substantial manifold pressure loss. The suction catheter device includes an envelope which is positioned around the catheter portion thereof in order to prevent contamination of catheter surfaces intended to be inserted into the patient's trachea and lungs.

Although this type of ventilator manifold and suction catheter device connection allows continuous respiratory support of the patient during suctioning of fluid from the patient, it nevertheless has several drawbacks associated with its use. For example, removal of the suction catheter device from the manifold, such as for the purpose of replacing the suction catheter device, or for attaching another accessory to the manifold (e.g., a manual resuscitation bag or a metered dose inhaler) cannot be accomplished without loss of internal manifold pressure and thereby a compromise of the integrity of the respiratory system. Further, separation of Hollister et al's suction catheter device from their suction control valve cannot be accomplished without opening the manifold to atmospheric pressure through the catheter. Therefore, replacement of either the suction catheter device or the suction control valve is not possible without loss of internal manifold pressure. Instead, respiratory support of the patient is compromised whenever the suction catheter device or the suction control valve is removed from the system for any reason. Since the suction catheter device tends to become contaminated relatively quickly with respect to the suction control valve and the ventilator manifold, it must be changed out of the system and replaced on a relatively frequent basis. However, because of the problems caused by loss of respiratory support during replacement, the ventilator manifold and/or the suction control valve are often prematurely discarded along with the suction catheter device in order to limit replacement time and the number of replacement procedures required.

U.S. Pat. No. 4,351,328 to Bodai attempts to solve one of the above problems by forming an opening in the ventilator manifold which is blocked by a pre-punctured resilient seal through which a catheter can be passed without substantially effecting the integrity of the system, i.e., without substantial gas exchange or pressure loss between the interior of the manifold and the atmosphere.

The Bodai device, although allowing entry and removal of a suction catheter through the ventilator manifold during continuous respiratory support of a patient, nevertheless fails to completely resolve the existing problems in the prior art. Specifically, the pre-punctured resilient material in Bodai's manifold opening allows only for the insertion of a catheter therethrough, and fails to accommodate a suction catheter device which includes a collapsible envelope which surrounds and seals the catheter against exterior surface contamination. Because of this, the suction catheter must be replaced after each use.

Further, there is no design consideration for the attachment of other accessory devices to the manifold, such as a manual resuscitation bag or a metered dose inhaler, which are often necessary for use in the care of a patient.

Also, the system described by Bodai tends to cause mucus and other fluids from the patient's lungs and trachea to collect in the manifold as the catheter is pulled past the pre-punctured resilient seal when being withdrawn. Because of this contamination problem, it is often necessary to replace the manifold on a more frequent basis than would otherwise be necessary, which necessitates a pressure breach in the support system.

There therefore exists a need in the art for a respiratory support system which includes a ventilator manifold which allows simple attachment and detachment of a suction catheter device therefrom during continuous patient respiratory support, without substantial pressure loss from the manifold and without substantial collection of body fluids in the manifold. There also exists a need in the art for a suction catheter device and a suction control valve which can be disassembled and reassembled, individually or collectively, from the respiratory support system during use thereof, and reassembled or replaced thereafter, without causing interior pressure loss from the ventilator manifold. There is a further need in the art to develop an improved apparatus for cleaning the suction catheter which inhibits the movement of liquid mucus secretions and/or catheter cleaning liquids into the manifold.

OBJECTS AND SUMMARY OF THE INVENTION

A principle object of the present invention is to provide a respiratory support system which allows attachment thereto and detachment therefrom of a suction catheter device without interruption of continuous patient respiratory support.

A further object of the present invention is to provide a suction catheter device which is designed to be capable of interchangeably engaging and disengaging a normally closed valve of a manifold port of a respiratory support system without compromising internal manifold pressure integrity.

Another object of the present invention is to provide a suction catheter device which is capable of being disassembled from the respiratory support system to allow replacement of the suction catheter device or a component part of the respiratory support system during respiratory support of a patient without compromising the integrity of the ventilator manifold.

A further object of the present invention is to provide a respiratory system having a ventilator manifold which includes an access port with a normally closed valve therein, which can accommodate an adaptor formed as part of the suction catheter which is designed to seal against and open the port, the normally closed valve allowing interchangeable use of suction catheters with the manifold while maintaining manifold pressure integrity.

Another object of the present invention is to provide a manifold for a respiratory system which includes an access port which is adapted to allow cleaning fluid to be injected into the adaptor in order to clean the adaptor and suction catheter while positioned within the access port without substantial movement of mucus or cleaning fluid into the manifold.

These and other objects of the present invention are realized in a presently preferred embodiment thereof, described by way of example and not necessarily by way of limitation, which provides for interchangeable use of components of a respiratory support system and a suction catheter device during respiratory support of a patient, without compromising the integrity of the respiratory support system through loss of internal pressure in the manifold thereof. The invention includes a ventilator manifold formed with an access port which includes a normally closed valve therein. The valve maintains the pressure differential between the atmosphere and the interior of the manifold regardless of manifold pressure fluctuations. The access port also includes a sleeve member positioned within the port, so as to line the port interior surface, which assists in sealing against an adaptor inserted into the port. The sleeve member also passes through a side opening in the port and attaches to a pigtail type fluid injection tube which is adapted for allowing injection of fluid therethrough into the access port and through the sleeve member into the adaptor. The pigtail may also include a one-way valve therein for preventing retrograde movement of fluid therethrough. The invention also includes a suction catheter device which includes a manifold-end connector having an adaptor formed to fit within the access port of the manifold and to sealingly engage therewith. Positioning the adaptor into the access port of the manifold forces a normally closed valve therein to an open position. The access port and adaptor may include a detent and stop-type locking arrangement for locking the adaptor within the port against inadvertent withdrawal thereof during use. The adaptor and access port include various designed openings therethrough which allow cleaning fluid to be injected into the interior of the adaptor to clean mucus from the catheter tip.

The manifold-end connector allows the catheter to pass freely therethrough and includes a window forming a magnifying lens which allows a user to view a magnified portion of the catheter positioned within the connector. The catheter itself may also include positioning marks thereon which, when viewed through the lens of the connector, inform the user of the position of the distal tip of the catheter relative to the connector so that the user can readily determine how far the catheter has been inserted into the patient's trachea or lungs, or conversely, how far the catheter has been withdrawn through the connector.

The suction catheter device also includes a valve-end connector which is designed to allow snap-in connection of an insert within the connector housing which will properly position both the end of the suction catheter and the catheter sleeve within the connector. The connector includes a septum which closes the end of the catheter against fluid flow therethrough until the suction control valve is properly attached to the connector. The suction control valve forces the septum open and allows fluid flow between the catheter and the suction control valve.

The suction control valve includes a main body forming a fluid flow channel therethrough and includes an actuator for opening and closing the fluid flow passage of the main body. The actuator is normally biased to a position in which the fluid flow passage is closed to prevent fluid passage therethrough and can be actuated by the user against the biasing thereof in order to open the fluid flow passage. The actuator may also be rotated relative to the valve body to a locked position in which the actuator can no longer be actuated to cause fluid flow through the valve.

DETAILED DESCRIPTION OF THE PREFERRED EMBODIMENTS

As shown in the exemplary drawings for the purposes of illustration, an embodiment of a manifold, suction catheter, and suction control valve of a respiratory support system made in accordance with the principles of the present invention, referred to generally by the reference numeral 10, is provided for interchangeable use of either the suction catheter or the suction control valve without interruption of respiratory support of the patient.

Figure 1:
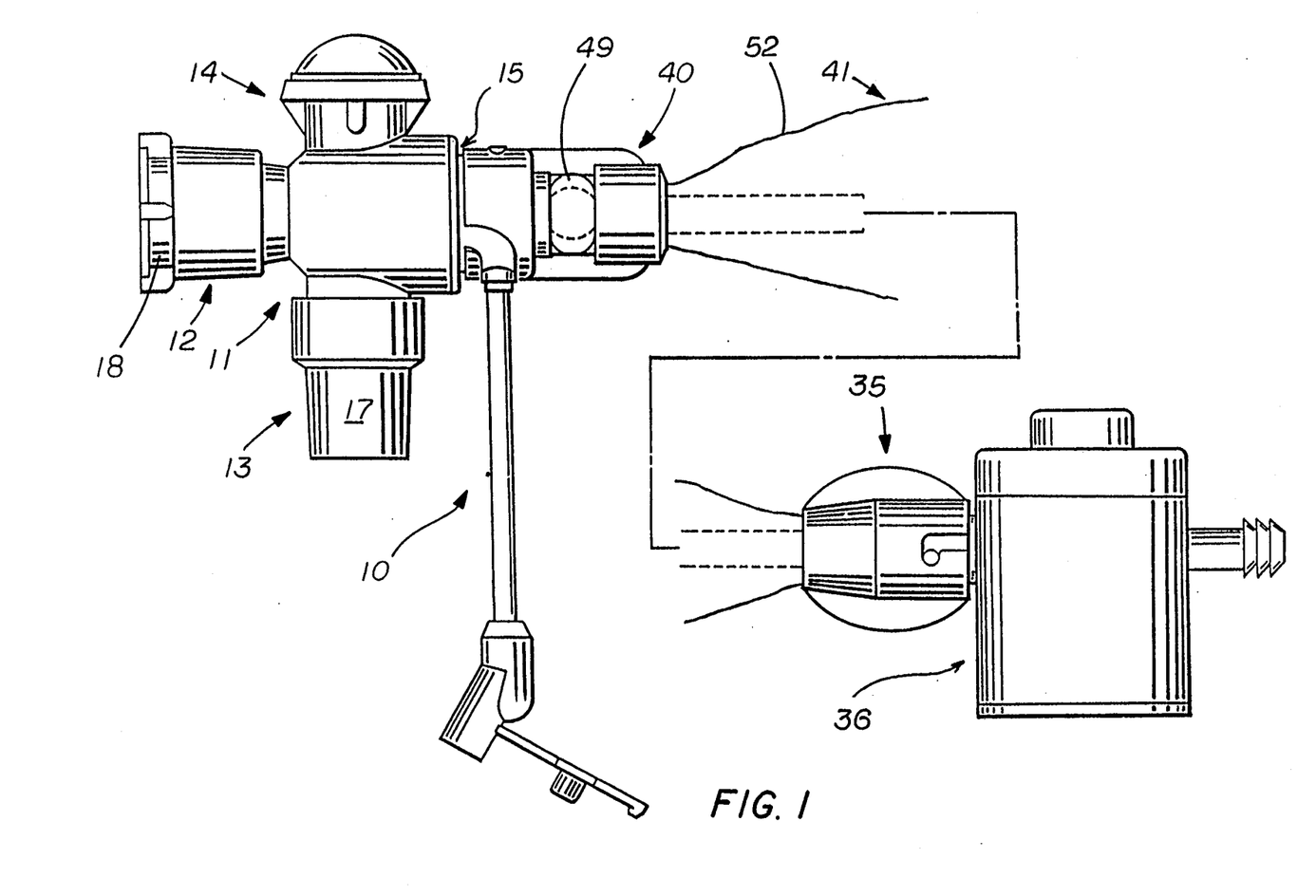
FIG. 1 shows a suction control valve and a manifold of a respiratory support system attached for use to a suction catheter device formed in accordance with the principles of the present invention.

More specifically, as shown in FIG. 1, the ventilator manifold 11 includes a plurality of access ports which facilitate its connection to a ventilator circuit being used by the patient. The manifold 11 is attached to a patient for fluid flow communication with the patient's lungs by the connection of the patient attachment port 12 thereof to the connector of an endotracheal tube assembly (not shown) which has been previously positioned in the trachea of a patient by any one of several well known procedures.

Ventilator circuit connection port 13 of the manifold 11 is designed for connection to flexible breathing hoses from the ventilator (not shown) in a well-known manner, such as through a "Y" site connector. Port 14 is normally capped and closed against air flow except for instances when nonpressurized ventilation is desired. The ventilator circuit provides a breathable gas mixture to the patient through one hose, and receives expelled air from the patient's lungs through another hose. The ventilator circuit further commonly includes various valves, regulators and the like associated with the hoses in order to effect respiration of the patient. The manifold 11, and hoses attached thereto at the ventilator circuit connection port 13, are generally made of disposable plastic material and are generally intended to be used by only one patient and then discarded.

When attached to the patient, the entire respiratory support system 10 is designed to isolate the patient's lungs from the atmosphere and allow pressurized forced ventilation of a gas mixture of a high oxygen content from the ventilator into the patient's lungs. Commonly ventilators of this type are used to maintain a positive end expiratory pressure (PEEP) within the ventilator manifold 11 and the patient's lungs at all times during exhalation. This technique is commonly used because of its benefit of supplying a minimum concentration of oxygen to the patient at all times for maintaining a proper blood oxygenation level. The PEEP procedure also keeps a large number of lung alveoli of the patient open at all times during respiratory support, thus increasing the effective lung area subject to ventilation.

Prevailing respiratory support techniques including PEEP, have made it very disadvantageous to interrupt respiratory support to the patient by opening the ventilator manifold to the atmosphere and thereby causing a loss of interior manifold pressure. Therefor, the necessary attachment of accessory devices to the system for medical procedures has been difficult due to the loss of isolation of the respiratory system from the atmosphere during these procedures, and the immediate loss of effective lung surface area due to collapse of the patient's lung alveoli. Further, when such procedures have been prolonged for any reason, the patient's blood oxygen has often dropped to inadequate levels, and subsequently forced overexertion of the patient's lungs and heart in order to return the blood oxygen level to normal. Also, disassembly and reassembly of the respiratory support system components for procedures with prior art accessory devices has often been a very time consuming procedure for the medical worker involved.

The present invention resolves the problems associated with loss of isolation of the respiratory support system from the atmosphere when accessory devices must be attached to the system in order to perform necessary medical procedures, or alternatively, when accessory devices must be replaced during respiratory support of a patient.

Specifically, the manifold 11 of the present invention includes an access port 15 which is in fluid flow communication with the interior of the manifold 11. The access port 15 includes a normally closed valve 16 (see FIG. 3) preferably made of a resilient material such as rubber or silicone which maintains the interior of the manifold 11 isolated from the atmosphere at all times. As explained above, the interior of the manifold 11, although experiencing constant pressure fluctuations, is generally kept at a pressure which is slightly above atmospheric pressure in order to properly administer oxygen according to the PEEP procedure.

The ventilator circuit connection port 13 and the patient attachment port 12 may, if desired, include swivel connectors 17 and 18 respectively thereon in order to allow relative rotation between the manifold 11 and the trachea tube and breathing hoses in order to isolate the trachea tube from the incidental forces causes by the manifold 11 or the breathing hoses attached thereto so as to increase the comfort of the patient.

Figure 2:
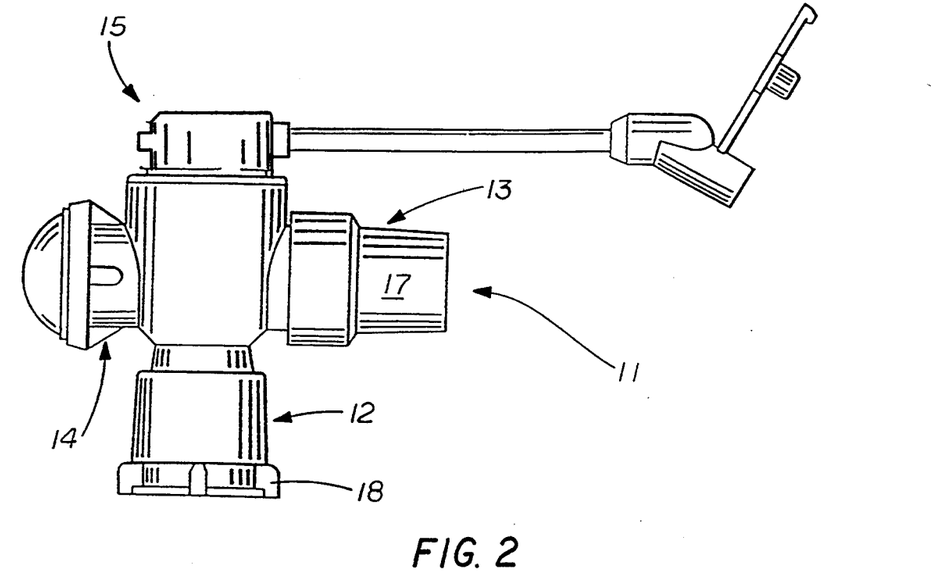
FIG. 2 is a side view of the ventilator manifold.
Figure 3:
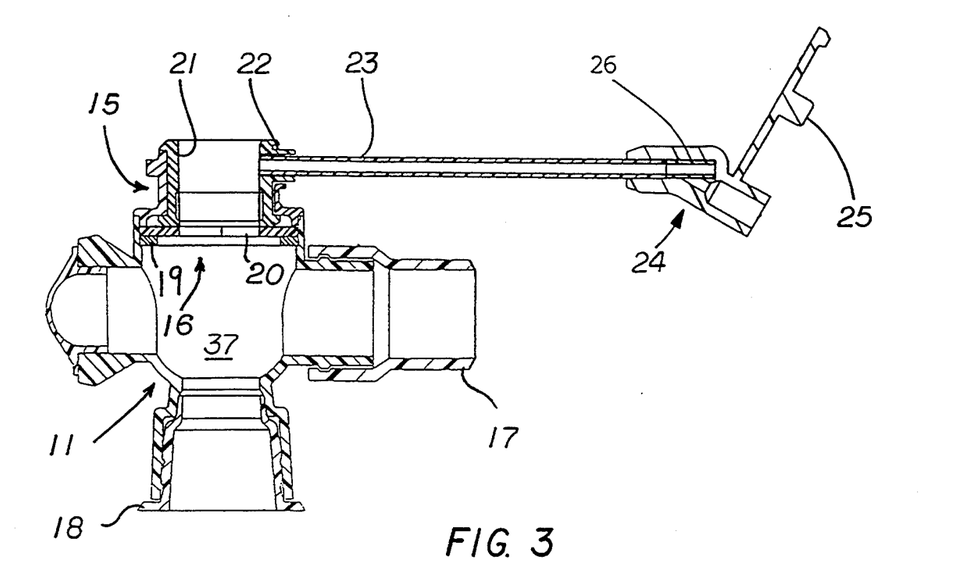
FIG. 3 is a cross-sectional view of the ventilator manifold shown in FIG. 2.
Figure 5:
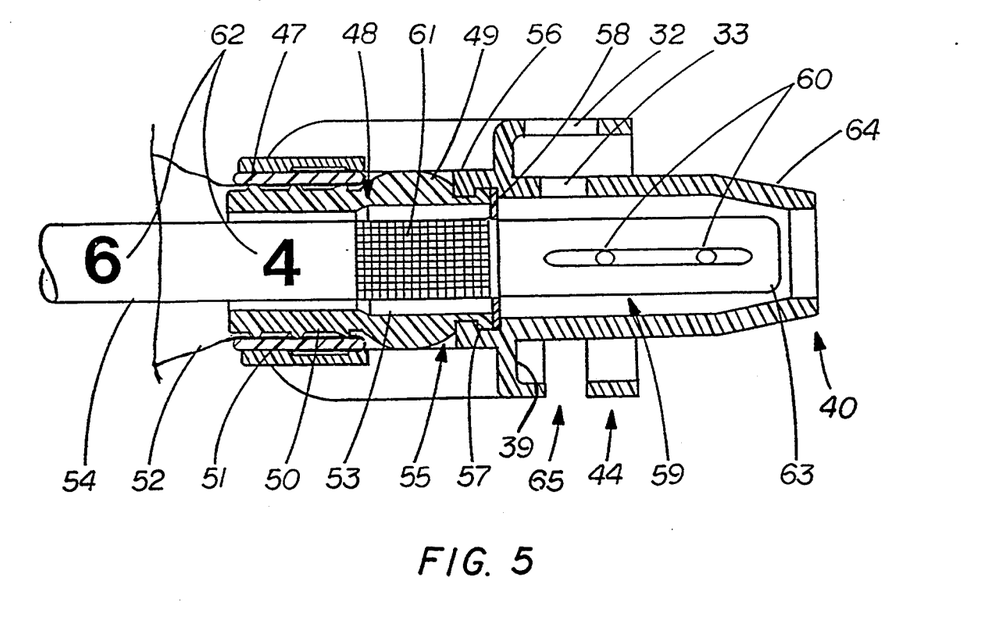
FIG. 5 is a cross-sectional view of the manifold-end connector of the suction catheter device shown in FIG. 4.

As best shown in FIGS. 2 and 3, the valve 16 is preferably formed to a circular disk shape and inserted into the manifold 11 between the access port 15 and a support ring 19. The valve 16 is formed with a slit, or a pair of perpendicular slits 20 which are normally closed against fluid flow therethrough, but may be forced opened by the insertion of the manifold end connector 40 therethrough (as shown in FIG. 5), of the suction catheter device 41 (see FIG. 1).

Figure 6:
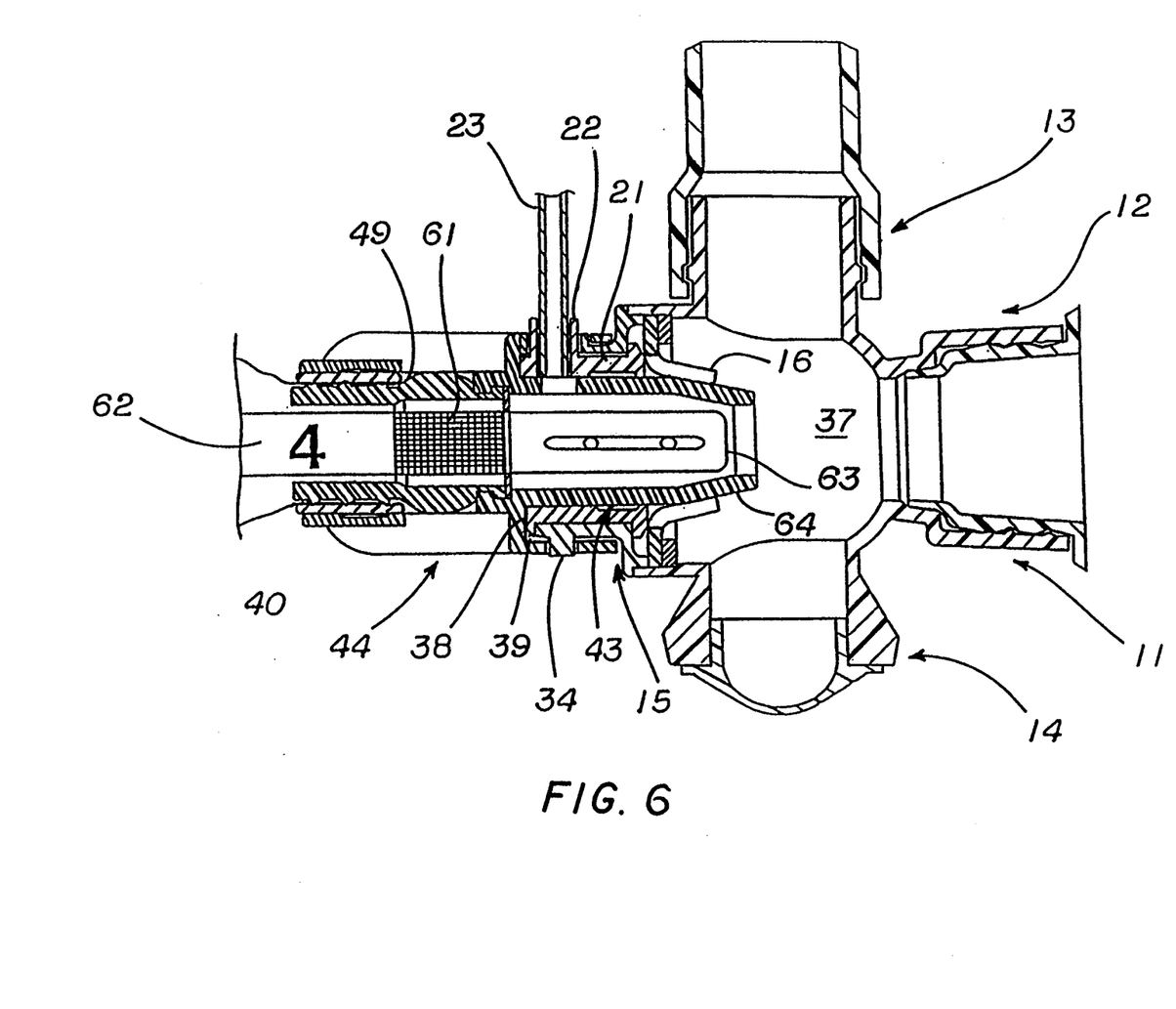
FIG. 6 is a cross-sectional view of the ventilator manifold with the manifold end connector of the suction catheter device attached to the access port thereof.

The interior of the access port 15 is lined with a sleeve member 21 which covers the entire interior surface of the access port 15 and abuts in sealing relationship against the normally closed valve 16. The interior diameter of the sleeve member 21 is predetermined to cause a snug fit with the manifold end connector 40 (as best shown in FIG. 6) to assist in the prevention of leakage from the manifold 11 when the normally closed valve 16 is forced opened by the manifold end connector 40.

The access port 15 forms a side opening 22 therethrough through which a portion of the sleeve 21 extends to be attached, such as by solvent bonding, to a pigtail fluid injection tube 23 which is intended for use in transporting fluid through the access port side opening 22 into the interior of the access port 15. The opposite end of the pigtail tube 23 includes preferably a luer connector 24 attached thereto with an integrally formed luer connector plug 25. A check valve 26, taking the form of a collapsible sleeve, may be positioned between the luer connector 24 and the pigtail tube 23 if desired, to collapse upon injection of fluid through the luer connector 24 into the pigtail tube 23, but expand to block fluid flow in the opposite direction.

It is preferred that the sleeve member 21 be formed of a relatively flexible material such as plasticized PVC, having good solvent bonding characteristics with the material forming the pigtail tube 23, the pigtail tube 23 preferably being formed of the same material as the sleeve member 21. The access port 15 according to the preferred embodiment of the present invention is preferably formed of a clear plastic, which is preferably the same material forming the main body of the manifold 11 in order to ensure good ultrasonic or solvent bonding therebetween.

Figure 4:
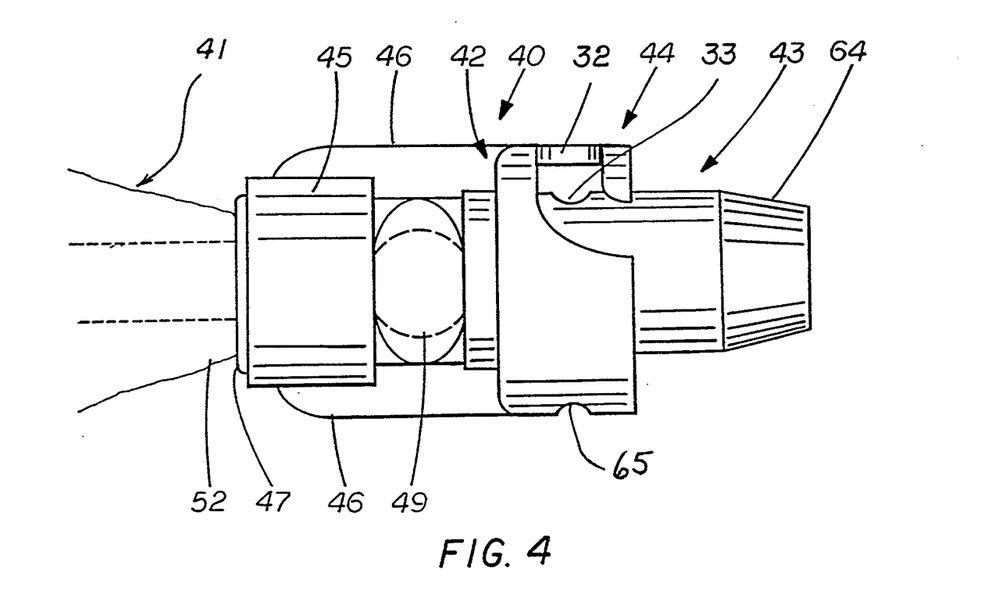
FIG. 4 is a plan view of a portion of the suction catheter device which includes the manifold-end connector thereof formed in accordance with the principles of the present invention.

Referring now to FIGS. 4 and 5, the manifold-end connector 40 of the suction catheter device 41 is shown. The connector 40 includes a unitary housing 42 which forms an adaptor 43, a locking mechanism 44, a base ring 45, and a plurality of rib members 46. The base ring 45 forms a generally cylindrical opening through which the sleeve attachment ring 47 can be inserted for frictional engagement to hold the sleeve 52 in proper position relative to the connector 40.

A magnifying insert 48 is formed as a generally cylindrical member having a bulbous lens 49 at one end thereof formed of clear plastic and a cylindrical extension 50 formed at the other end thereof. The cylindrical extension 50 is formed to a slightly smaller diameter than the sleeve attachment ring 47 and may include ribbing 51 around the exterior surface thereof to aid in frictional engagement between the extension 50 and the sleeve attachment ring 47. When constructed for use, the sheath 52 is positioned around the sleeve attachment ring 47 so as to be frictionally engaged between the extension 50 and the interior surface of the sleeve attachment ring 47, and wrapped around at least a portion of the exterior surface of the sleeve attachment ring 47 to also become frictionally engaged with the base ring 45 when the sleeve attachment ring 47 is inserted therein.

The lens 49 of the magnifying insert 48 is preferably formed of a substantially clear plastic which magnifies the portion of the catheter 54 for viewing by a user through the generally cylindrical opening or window 55 formed by the unitary housing 42 between the base ring 45 and the locking mechanism 44. The window 55 extends around the entire circumference of the unitary housing 42 and allows viewing of the lens 49 by a user at any viewing angle except where the window 55 may be slightly covered by a portion of the ribbed members 46 which extend between the base ring 45 and the locking mechanism 44.

The unitary housing 42 also includes an annular locking shoulder 56 which operates in conjunction with an annular locking shoulder 57 on the magnifying insert 48 to secure the magnifying insert 48 in proper position within the unitary housing 42, and to ensure an air-tight seal therebetween and with the sealing ring 58.

The magnifying insert 48 has a generally cylindrical passageway 53 formed therethrough which is of slightly larger diameter than the catheter 54 and which allows uninhibited movement of the catheter 54 therethrough.

If desired, the catheter 54 may be formed with a tip 59 of softer material than the remainder of the catheter 54 and which may include side openings 60 therein. The catheter 54 may also include a series of markings such as ring marking 61 and/or number markings 62 along the length thereof which will tend to be magnified when located beneath the lens 49. The marking 61 is intended to indicate the completely withdrawn position of the catheter 54 into the adaptor 43.

For example, in operation, the user can withdraw the catheter 54 through the manifold-end connector 40 until the ring marking 61 moves into view within the lens 49. Positioning of the ring marking 61 beneath the lens 49 indicates to the user that the catheter 54 has been withdrawn the entire recommended distance through the connector 40 and cannot be further withdrawn without risking inadvertent passage of the side openings 60 of the catheter 54 past the sealing ring 58, which would effectively allow leakage of air past the sealing ring 58. As is readily evident, an even greater leakage of air would occur if withdrawal of the catheter 54 continued until the distal end 63 thereof passed through the sealing ring 58 or through the connector 40 entirely.

The number markings 62 may be positioned along the catheter 54 so as to indicate to the user a particular predetermined distance which the distal end 63 thereof extends beyond the connector 40. As each number marking 62 appears in the lens 49, the user can recognize the number as corresponding to a particular predetermined distance that the distal end 63 is extending beyond the connector 40. In this manner, when the connector 40 is attached to the manifold 11 of the respiratory support system 10, the user can readily determine how far down a patient's trachea or lungs the catheter 54 has been inserted during an aspiration procedure by noting the particular number marking 62 visible through the lens 49.

The adapter 43 and locking mechanism 44 of the connector 40 operate to attach the connector 40 to the ventilator manifold 11. As best shown in FIG. 6, attachment of the connector 40 to the manifold 11 is effected by insertion of the adapter 43 into the access port 15 until the tapered top section 64 thereof engages the valve 16 and forces it toward the interior of the manifold 11. Upon complete insertion of the adapter 43 into the access port 15, the valve 16 is completely open.

In reference to FIGS. 5 and 6, the locking mechanism 44 of the connector 40 is formed to encircle a portion of the adapter 43 and may include a pair of arcuate slots 65 and 32 which operate together to ensure secure attachment of the connector 40 to the access port 15 of the manifold 11, and also ensure proper relative orientation between the adapter 43 and the access port 15, to cause the injection fluid opening 33 of the adapter 43 to be positioned in alignment with the side opening 22 of the access port 15 when the adapter 43 is properly locked in position therein for use. The arcuate slot 65 is sized to be engageable with the nub 34 which is located directly opposite the side opening 22 on the access port 15. The arcuate slot 32 is larger in width than the arcuate slot 65 and therefore can accommodate the side opening 22 of the access port 15. As is readily evident, the adapter 43 can only be locked in position within the access port 15 in one unique relative orientation in which the injection fluid opening 33 and the side opening 22 are in alignment.

As best shown in FIG. 6, attachment of the manifold-end connector 40 to the respiratory manifold 11 is effected by insertion of the adaptor 43 into the access port 15 until the tapered top section 64 engages the valve 16 and forces it toward the interior of the manifold 11. Upon complete insertion of the adaptor 43 into the port 15, the valve 16 is completely open and the elastic sleeve member 21 sealingly engaged with the adaptor 43. Also, the sleeve shoulder 38 of the sleeve member 21 is forced to resiliently deform within the base 39 of the locking mechanism 44. This increases the air tight seal and assists in positively locking the adaptor 43 to the access port 15 by forcing the arcuate slots 65 and 32 against the nub 34 and side opening 22 respectively.

It is intended that during insertion of the adaptor 43 into the access port 15, the sealing relationship formed between the sleeve member 21 and the adaptor 43 commence prior to opening of the valve 16 by the tapered top section 64, in order to ensure isolation of the interior of the manifold 11 from the atmosphere during attachment of the suction catheter device 41. Once completely inserted within the port 15, the tapered top section 64 extends completely through the access port 15 and into the manifold central chamber 37.

As shown in FIG. 6, the pigtail tube 23 can be used to inject fluid into the adaptor 43 to clean the suction catheter 54 and the sealing ring 58 of mucal materials which may have accumulated therein due to repeated insertion and withdrawn of the catheter 54 from the patient's lungs during aspiration procedures. The cleaning fluid can then be aspirated through the catheter 54 to remove it from the interior of the adaptor 43. Since the mucus and cleaning fluid around catheter 54 is mainly contained within the adaptor 43, the control chamber 37 of the manifold 11 is not subjected to the accumulation of fluid therein which can cause premature contamination and necessitate premature replacement.

Operation of the respiratory support system 10 is preferably as follows. First, the ventilator manifold 11 is attached to the tracheal tube which has previously been inserted into the patient's trachea, and the ventilator circuit of the respiratory support system is attached to the manifold 11 in a well-known manner. The manifold-end connector 40 of the suction catheter device 41 is then inserted into the access port 15 of the manifold 11 and rotated to its above-described locking position therewith. Any well known suction control valve 36 can then be attached to the valve-end connector 35 and then attached to a source of suction pressure in a well-known manner.

When it is desired to suction the patient's trachea or lungs, the catheter 54 is advanced through the manifold-end connector 40, the manifold 11, and the tracheal tube into the patient's trachea and lungs any desired distance (which can be monitored by viewing the number markings 62 which appear through the lens 49 of the connector 40). Aspiration of the patient's trachea and lungs is then performed in the well known manner.

When suctioning is completed, the catheter 54 is withdrawn until the medical worker can view the ring marking 61 through the lens 49. The medical worker may then clean the distal end of the catheter 54 by injecting fluid through the access port side opening 22 and the injection fluid opening 33 into the adapter 43, and subsequently suctioning the fluid through the catheter 54.

When it becomes necessary to remove the suction catheter device 41 from the manifold 11, the manifold-end connector 40 is merely detached from the access port 15 and withdrawn therefrom. No loss of PEEP from the manifold 11 occurs due to the automatic reclosure of the normally closed valve 16.

Figures 7, 8:
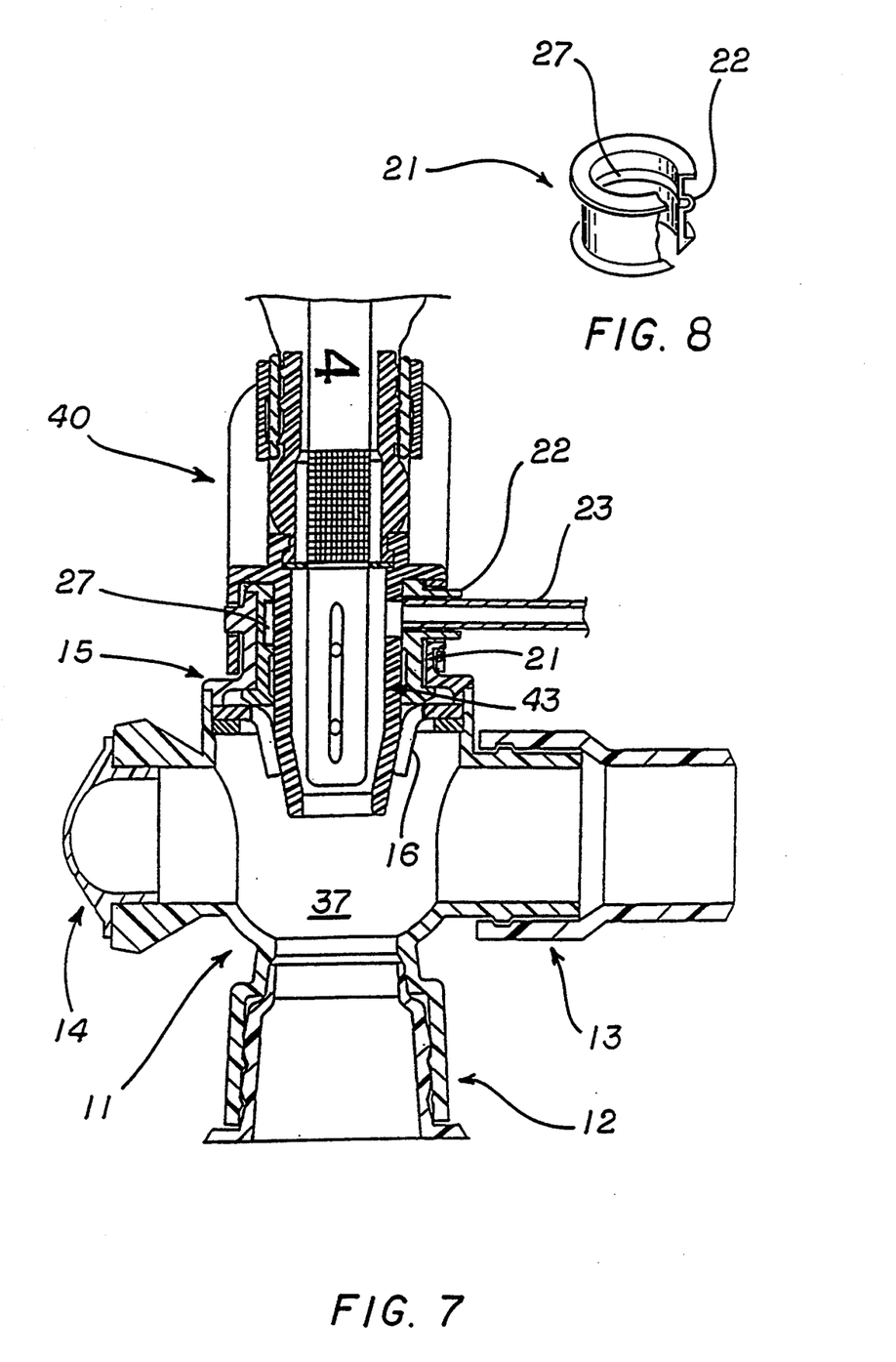
FIG. 7 is a cross-sectional view of a second preferred embodiment of the invention showing the manifold end connector of the suction catheter device attached to the access port of the ventilator manifold.
FIG. 8 is a cut away view of the second preferred embodiment of the sleeve of the access port.

Alternatively, as shown in FIGS. 7 and 8, a second preferred embodiment of the present invention includes a modification to the sleeve member 21 which improves the transfer of fluid from the pigtail tube 23 into the adaptor 43. The modification includes an annular groove 27 positioned around the interior of the sleeve member 21 adjacent the side opening 22 thereof. In this embodiment, fluid injected through the pigtail 23 can pass into the annular groove 27 and completely surround a portion of the adaptor 43. In this manner, it is not necessary that the injection fluid opening 33 of the adaptor 43 be in perfect alignment with the side opening 22 in order for injected fluid to pass therethrough into the interior of the adaptor 43.

Figure 9:
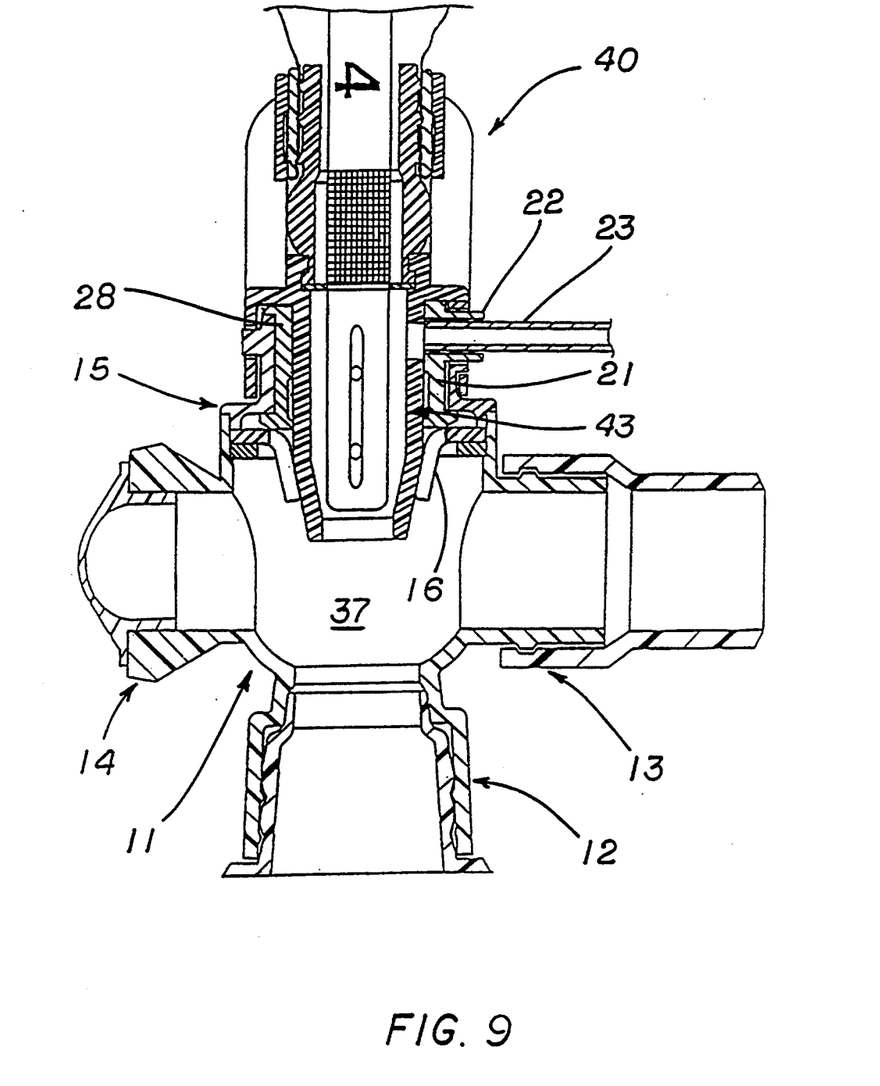
FIG. 9 is a cross-sectional view of a third preferred embodiment of the present invention showing the manifold end connector of the suction catheter device attached to the access port of the ventilator manifold.
Figure 10:
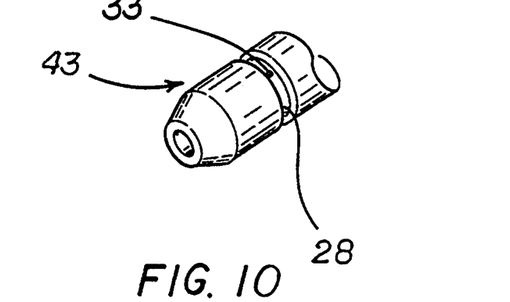
FIG. 10 is a perspective view of the third preferred embodiment of the adaptor of the manifold end connector of the present invention.

FIGS. 9 and 10 disclose a third preferred embodiment of the present invention which includes a modification to the adaptor 43 in the form of an annular groove 28. The annular groove 28 encircles the outside of the adaptor 43 at a position directly adjacent the injection fluid opening 33 thereof. As can be seen in FIG. 9, when fluid is injected through pigtail tube 23 it can pass completely around the adaptor 43 through annular groove 28. In this manner, should the adaptor 43 be misaligned when attached to the manifold 11, fluid will nevertheless be able to pass around the adaptor until it can move through the injection fluid opening 33 thereof into the adaptor's interior.

Figure 11:
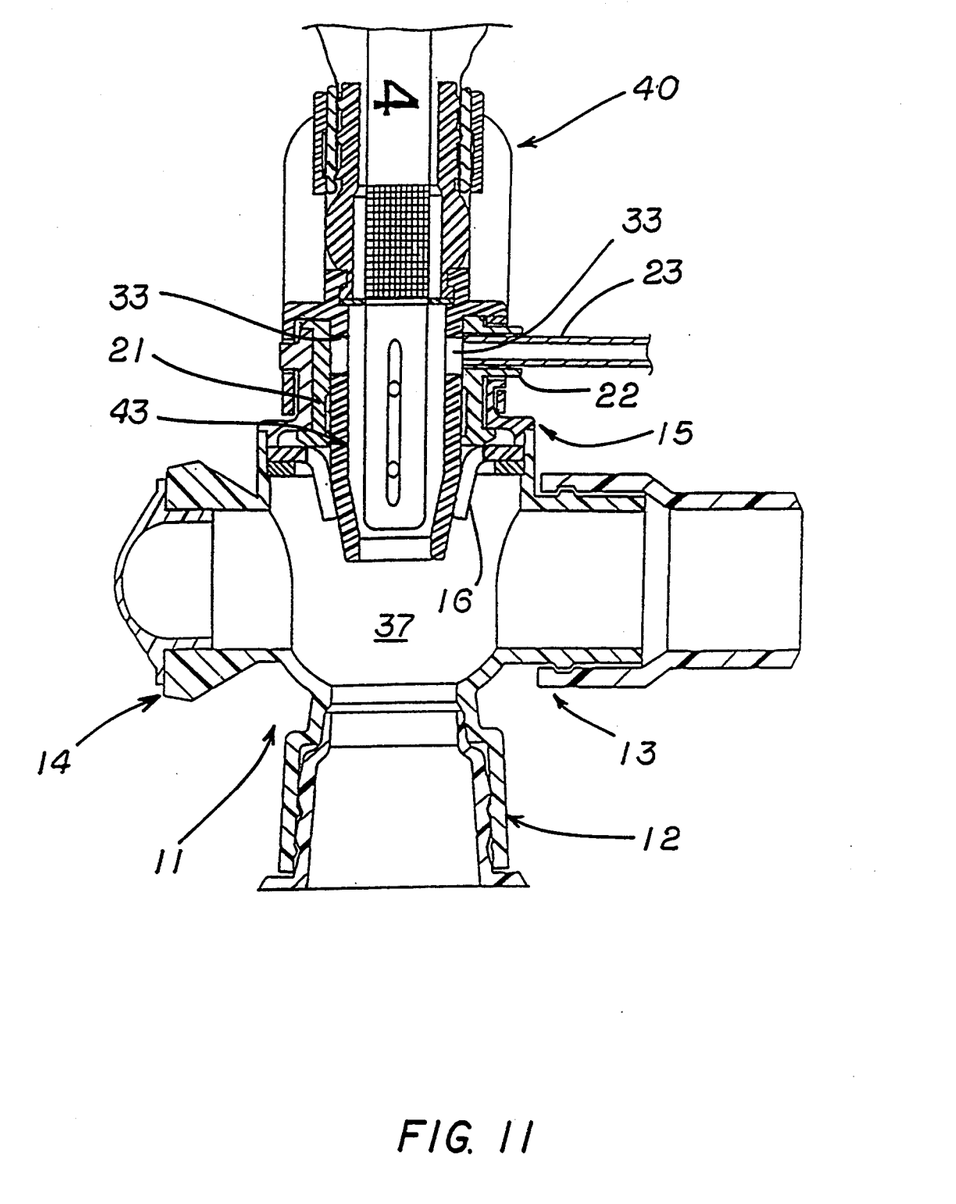
FIG. 11 is a cross-sectional view of the fourth preferred embodiment of the present invention showing the manifold end connector of the suction catheter device attached to the access port of the ventilator manifold.

A fourth preferred embodiment of the present invention is shown in FIG. 11 in which the adaptor 43 is modified to include a plurality of injection fluid openings 33 which are uniformly spaced apart around the adaptor 43 in a manner predetermined to ensure that one of the injection fluid openings 33 is aligned with the pigtail tube 23 when the adaptor 43 is attached to the manifold port 15. In this embodiment of the invention, it is preferred that at least two injection fluid openings 33 be positioned around the adaptor 43 at diametrically opposed positions. If desired, it is also within the scope of this embodiment of the present invention to provide four injection fluid openings 33 each positioned at 90° intervals around the adaptor 43. It is also within the scope of this embodiment of the invention to provide any number of injection fluid openings 33 around the adaptor 43 in uniformly spaced positions to ensure alignment of at least one of the injection fluid openings 33 with the pigtail tube 23.

Figure 12:
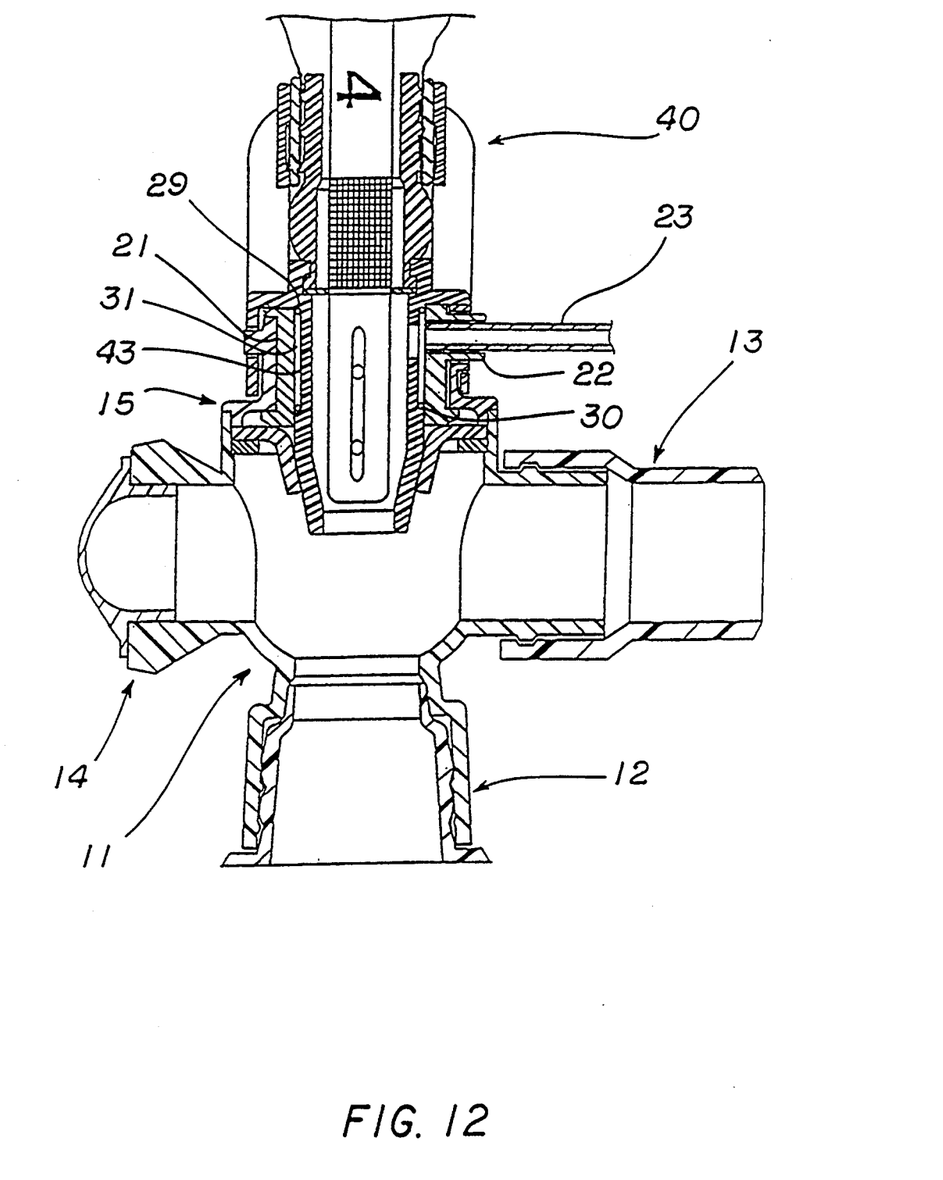
FIG. 12 is a cross-sectional view of a fifth preferred embodiment of the invention showing the manifold end connector of the suction catheter device attached to the access port of the ventilator manifold.

FIG. 12 shows a fifth preferred embodiment of the present invention in which the adaptor 43 includes a proximal sealing ring 29 and a distal sealing ring 30 which entirely encircle the adaptor 43. The sealing rings 29 and 30 seal against the interior of the sleeve member 21 when the adaptor 43 is positioned in the port 15. In this preferred embodiment of the invention, the external diameter of the adaptor 43 is slightly smaller than the internal diameter of the sleeve member 21, and the sealing rings 29 and 30 extend to a slightly greater diameter than the adaptor 43 and seal against the sleeve member 21 as shown. When the adaptor 43 is positioned within the port 15, an annular clearance area or cavity 31 is formed between the sleeve member 21 and the outer surface of the adaptor 43. Fluid injected through the pigtail tube 23 can then enter the cavity 31 and is prevented from leaking past the adaptor 43 by the sealing rings 29 and 30. In this manner, should the injection fluid opening 33 be misaligned with the pigtail tube 23, fluid can nevertheless flow through the injection fluid opening 33 by passing into the cavity 31 and pass around the adaptor until it reaches the injection fluid opening 33.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

We claim:

1. A respiratory support system comprising:
   an adaptor formed as part of a respiratory system accessory device, said adaptor including an injection fluid opening therein,
   a manifold adapted to be connected for fluid flow attachment between a patient and a ventilator circuit said manifold including an injection fluid inlet opening therein, said manifold including an accessory access port for allowing attachment of said adaptor to said manifold, said accessory access port being normally closed against fluid flow therethrough, said accessory access port further including an injection fluid inlet opening therein, and
   said adaptor further including means for opening said accessory access port in response to attachment of said adaptor to said accessory access port to allow fluid flow access between said manifold and said respiratory system accessory device,
   means interconnecting said adaptor and said manifold such that, when said adaptor is positioned in said accessory access port of said manifold, said injection fluid inlet opening is in fluid communication with said injection fluid opening of said adaptor regardless of the relative rotational orientation of said adaptor and said manifold, whereby fluid can be injected through said injection fluid inlet opening and said injection fluid opening into said adaptor.

2. A respiratory support system according to claim 1 wherein said adaptor includes at least a proximal sealing surface and a distal sealing surface, said proximal and distal sealing surfaces operating to form a seal against said accessory access port when said adaptor is positioned therein, said accessory access port and said adaptor between said proximal and distal sealing surfaces forming a cavity which is in fluid flow communication with said injection fluid inlet opening in said manifold and said injection fluid opening in said adaptor.

3. A respiratory support system according to claim 2 wherein said proximal and distal sealing surfaces include O-rings.

4. A respiratory support system according to claim 2 wherein said adaptor includes an annular groove therein which forms a substantial portion of said cavity, said injection fluid opening in said adaptor being positioned in said annular groove.

5. A respiratory support system according to claim 2 wherein said accessory access port includes an annular groove formed therein which forms a substantial portion of said cavity, said injection fluid inlet opening of said manifold being located in said annular groove.

6. A respiratory support system according to claim 5 wherein said accessory access port includes an elastomeric sleeve member formed therein, which operates to seal against said adaptor when said adaptor is positioned in said accessory access port, and said annular groove and said injection fluid inlet opening being formed in said elastomeric sleeve.

7. A respiratory support system according to claim 2 wherein said adaptor includes a plurality of injection fluid openings therein.

8. A respiratory support system according to claim 7 wherein said plurality of injection fluid openings in said adaptor are uniformly spaced around a circumference of said adaptor.

9. A respiratory support system according to claim 1 wherein said accessory access port includes a normally closed valve therein which is closed against fluid flow therethrough and is forced to an open position in response to attachment of said adaptor to said accessory access port.

10. A respiratory support system according to claim 1 further including means for locking said adaptor to said accessory access port.

11. A respiratory support system according to claim 1 wherein said adaptor is formed of a generally hollow tubular member having a proximal end and a distal end, said proximal end being attachable to a respiration system accessory, and said distal end including means for opening said normally closed accessory access port.

12. A respiratory support system according to claim 1 wherein the respiratory system accessory device is a suction catheter device.

* * * * *